(12) United States Patent
Mirza et al.

(10) Patent No.: US 11,224,455 B2
(45) Date of Patent: Jan. 18, 2022

(54) ENDOSCOPIC HOOK BLADE AND USE THEREOF

(71) Applicant: A.M. SURGICAL, INC., Smithtown, NY (US)

(72) Inventors: Ather Mirza, Smithtown, NY (US); Romi Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 137 days.

(21) Appl. No.: 15/585,031

(22) Filed: May 2, 2017

(65) Prior Publication Data

US 2018/0014843 A1 Jan. 18, 2018

Related U.S. Application Data

(60) Continuation of application No. 14/820,881, filed on Aug. 7, 2015, which is a division of application No. 14/059,170, filed on Oct. 21, 2013, now abandoned, which is a continuation of application No. 13/230,506, filed on Sep. 12, 2011, now abandoned.

(51) Int. Cl.
| | |
|---|---|
| *A61B 17/32* | (2006.01) |
| *A61B 1/018* | (2006.01) |
| *A61B 1/00* | (2006.01) |
| *A61B 1/04* | (2006.01) |
| *A61B 1/317* | (2006.01) |
| *A61B 90/00* | (2016.01) |

(52) U.S. Cl.
CPC .. *A61B 17/320016* (2013.01); *A61B 1/00087* (2013.01); *A61B 1/018* (2013.01); *A61B 1/04* (2013.01); *A61B 1/317* (2013.01); *A61B 17/320036* (2013.01); *A61B 90/06* (2016.02); *A61B 2090/061* (2016.02)

(58) Field of Classification Search
CPC .... A61B 17/320016; A61B 17/320036; A61B 17/295; A61B 17/3213; A61B 18/1442; A61B 17/32; A61B 2017/00349; A61B 2017/00464; A61B 2017/320044
See application file for complete search history.

(56) References Cited

U.S. PATENT DOCUMENTS

| | | | | |
|---|---|---|---|---|
| 1,398,850 A | * | 11/1921 | Franco | A01B 1/16 7/114 |
| 1,500,402 A | * | 7/1924 | Lewis | B26B 5/00 279/105.1 |

(Continued)

*Primary Examiner* — Elizabeth Houston
*Assistant Examiner* — Lindsey Bachman
(74) *Attorney, Agent, or Firm* — Bodner & O'Rourke, LLP; Gerald T. Bodner; Christian P. Bodner

(57) ABSTRACT

An endoscopic surgical blade is disclosed. The blade is of a hook design, having an upper cutting surface located on the trailing edge of an arm and a lower cutting surface on the upper edge of the main body of the blade. The blade is part of an endoscopic knife assembly which also contains a knife tube and alignment ring. The endoscopic knife assembly is for use in endoscopic surgery by insertion of the assembly through a slotted cannula. The knife tube is hollow and allows the insertion of an endoscope for viewing of the surgical procedure. A method for a performing an operative procedure on a target tissue in a subject using an endoscopic knife assembly having a hook blade is also described.

10 Claims, 4 Drawing Sheets

(56) References Cited

U.S. PATENT DOCUMENTS

| | | | | |
|---|---|---|---|---|
| 2,049,898 | A | * | 8/1936 | Driest ................ A61B 17/3213 279/43 |
| 2,676,595 | A | * | 4/1954 | Elith ....................... A61D 1/00 30/353 |
| 3,834,393 | A | * | 9/1974 | Goggins ............ A61B 17/1604 30/277 |
| 5,366,465 | A | * | 11/1994 | Mirza ............ A61B 17/320036 128/898 |
| 5,578,051 | A | * | 11/1996 | Mirza ............ A61B 17/320036 128/898 |
| 2005/0203523 | A1 | * | 9/2005 | Wenstrom, Jr. .... A61B 17/1675 606/79 |
| 2010/0286719 | A1 | * | 11/2010 | Paul .................. A61B 17/3207 606/159 |

\* cited by examiner

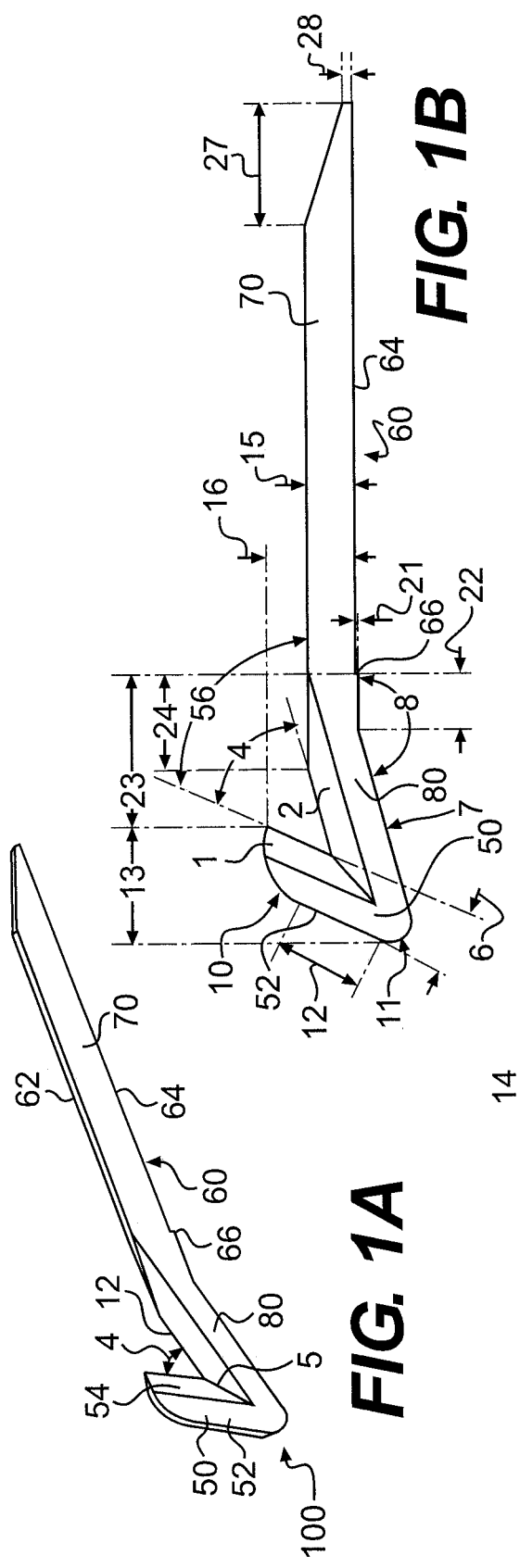
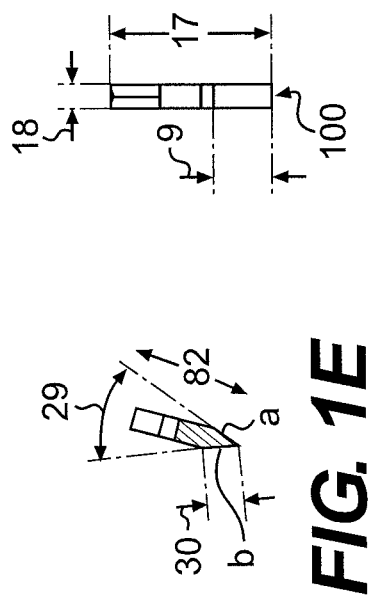
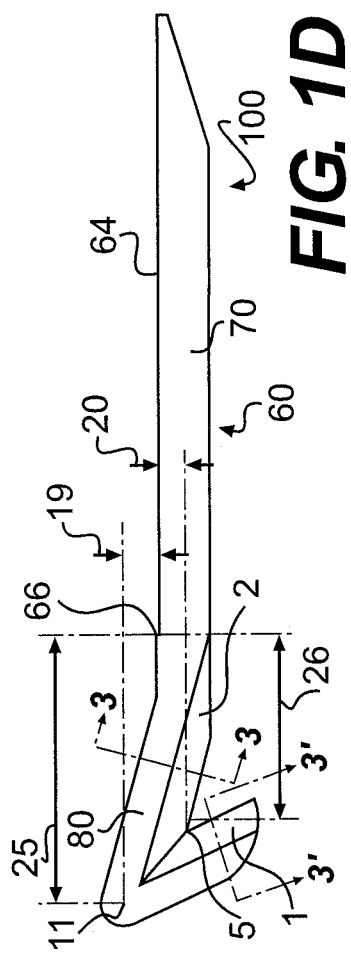

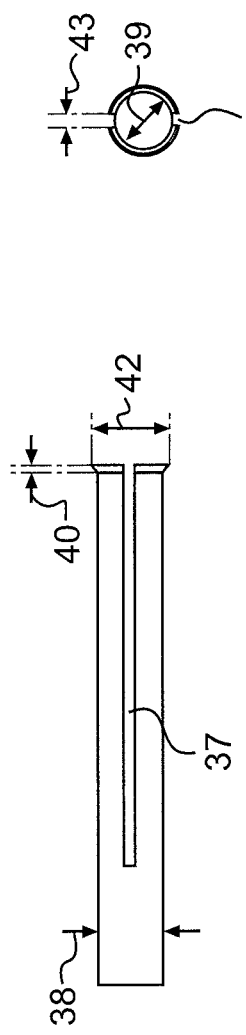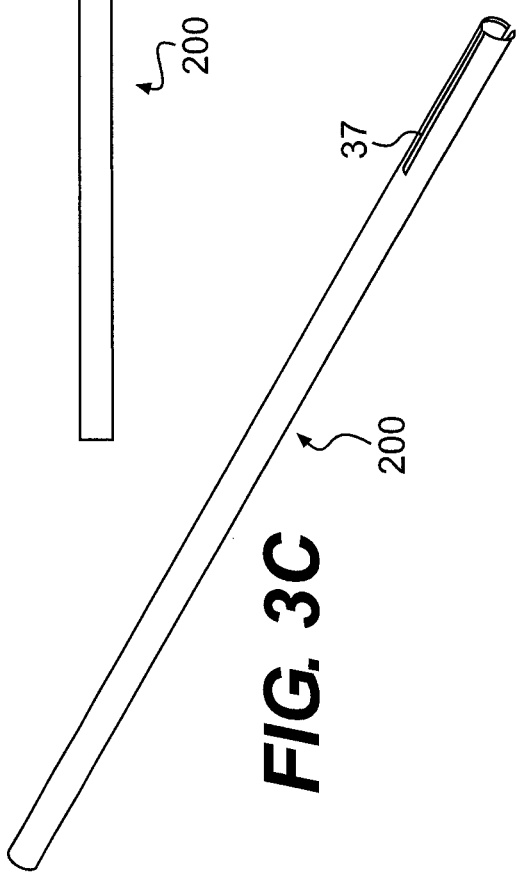
FIG. 3A
FIG. 3B
FIG. 3C
FIG. 3D
FIG. 3E

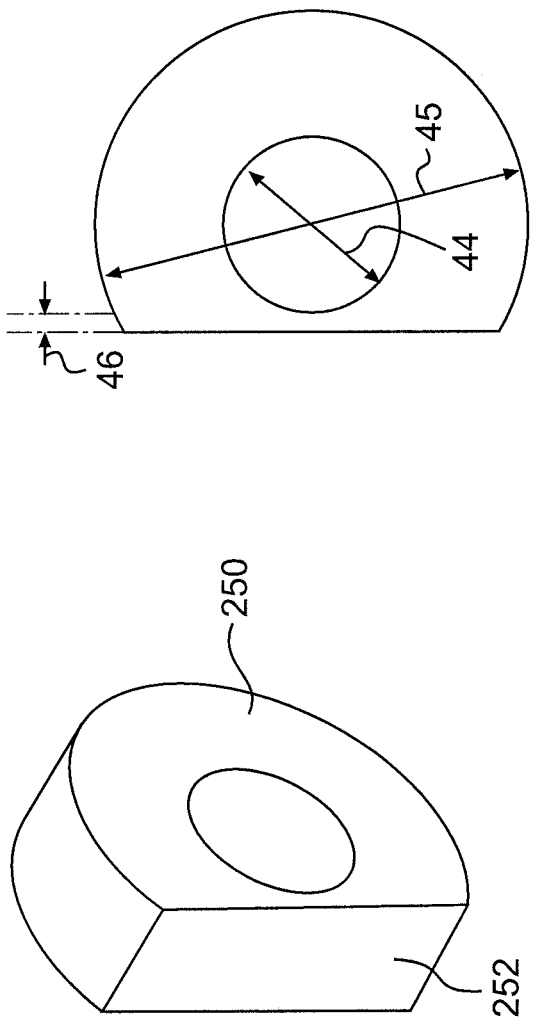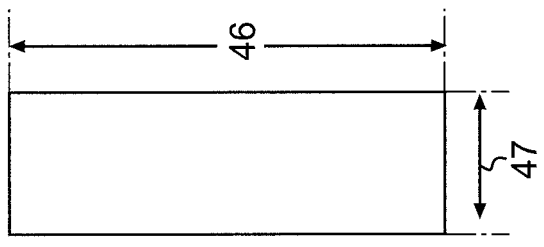

ENDOSCOPIC HOOK BLADE AND USE THEREOF

This application is continuation of U.S. patent application Ser. No. 14/820,881, filed Aug. 7, 2015, which is a divisional application of U.S. patent application Ser. No. 14/059,170, filed Oct. 21, 2013, which is a continuation of U.S. patent application Ser. No. 13/230,506, filed Sep. 12, 2011, the entirety of which is incorporated herein by reference.

FIELD

The present application relates to medical devices and, in particular, to a surgical blade for endoscopic operations.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Among more recent developments and advances in endoscopic surgical procedures, arthroscopic surgery employing the use of endoscopic devices has found widespread application. For example, endoscopic procedures have been used in effectuating carpal tunnel release with endoscopic instruments. However, there always exists a need to further improve the utility of the instrument, reduce the cost and improve the performance of endoscopic surgical procedures.

SUMMARY

One aspect of the present application relates to a hook blade for an endoscopic knife assembly. The hook blade comprises an arm having a forward edge, a trailing edge and an upper cutting surface located on the trailing edge; a main body having an upper edge, a lower edge, a distal section, a proximate section, and a lower cutting surface located on the upper edge of the distal section; wherein the distal section of the main body angles downward from the proximate section of the main body, forming a downward angle with the proximate section of the main body, wherein the arm protrudes from the distal section of the main body and extends back towards the main body in a hook-like manner, forming a hook angle with the proximate section of the main body, and wherein the upper cutting surface and the lower cutting surface meets at a crotch forming a cutting angle between the two cutting surfaces.

Another aspect of the present application relates to an endoscopic knife assembly. The endoscopic knife assembly comprises a knife tube having a distal end and a proximate end, a hook blade attached to the distal end, and an alignment ring attached near the proximate end.

Yet another aspect of the present application relates to an instrument kit for implementing an endoscopic surgical procedure. The instrument kit comprises a slotted cannula for endoscopic surgical procedures and an endoscopic knife assembly comprising a hook blade, a knife tube and an alignment ring. The endoscopic knife assembly is insertable into the slotted cannula.

Still another aspect of the present application relates to a method for a performing an operative procedure on a target tissue in a subject, comprising: making an incision to establish an entry portal, inserting a cannula having open proximal and distal ends, inserting an endoscope into the cannula, said endoscope comprising an endoscopic knife assembly having a hook blade, advancing said endoscope so that the hook blade moves distal to and is in contact with the target tissue, operatively engaging the target tissue with the hook blade, and withdrawing the hook blade back towards the cannula to perform the operative procedure on the target tissue.

BRIEF DESCRIPTION OF THE DRAWINGS

The present application can be better understood by reference to the following drawings. The drawings are merely exemplary to illustrate certain features that may be used singularly or in combination with other features and the present application should not be limited to the embodiments shown.

FIGS. 1A-F illustrate a hook blade component of an endoscopic knife assembly. FIG. 1A is a perspective view showing the hook blade component. FIG. 1B depicts a side view of the hook blade component, showing the cutting surfaces, the transition where the blade is joined to the knife tube and the taper at the end of the blade. FIG. 1C is a perspective view showing a top view of the hook blade. FIG. 1D depicts a side view of the hook blade component. FIG. 1E is a cross section view of the hook blade at the bisecting line 3 in FIG. 1D depicting an exemplary angle of a cutting surface of the blade component. FIG. 1F is a perspective view of the hook blade from the back depicting the width of the blade, the transition and the extension of the lower cutting surface below the transition.

FIG. 2A is a perspective view of the endoscopic knife assembly from the side. FIG. 2B is a perspective view of the endoscopic knife assembly from the top. FIG. 2C is a perspective view of the endoscopic knife assembly from the bottom. FIG. 2D is a perspective view of the endoscopic knife assembly from the front.

FIGS. 3A-E illustrate the knife tube component of the endoscopic knife assembly. FIG. 3A is a magnified view from the side of the proximate end of a knife tube, showing the slots and the flared end. FIG. 3B is a perspective view of the proximate end of a knife tube, showing the slots and the flared end. FIG. 3C is a perspective view from the bottom of a knife tube, shown at an angle. FIG. 3D is a perspective view from the side of a knife tube. FIG. 3E is a perspective view from the top or bottom of a knife tube.

FIGS. 4A-D illustrate the alignment ring component of the endoscopic knife assembly. FIG. 4A is a perspective view at an angle as seen from the bottom, showing the flattened bottom face of the alignment ring. FIG. 4B is a perspective view at an angle as seen from the front or back face of the alignment ring. FIG. 4C is a perspective view seen from the side of the alignment ring. FIG. 4D is a perspective view seen from the top of the alignment ring.

DETAILED DESCRIPTION

Figure 2A:
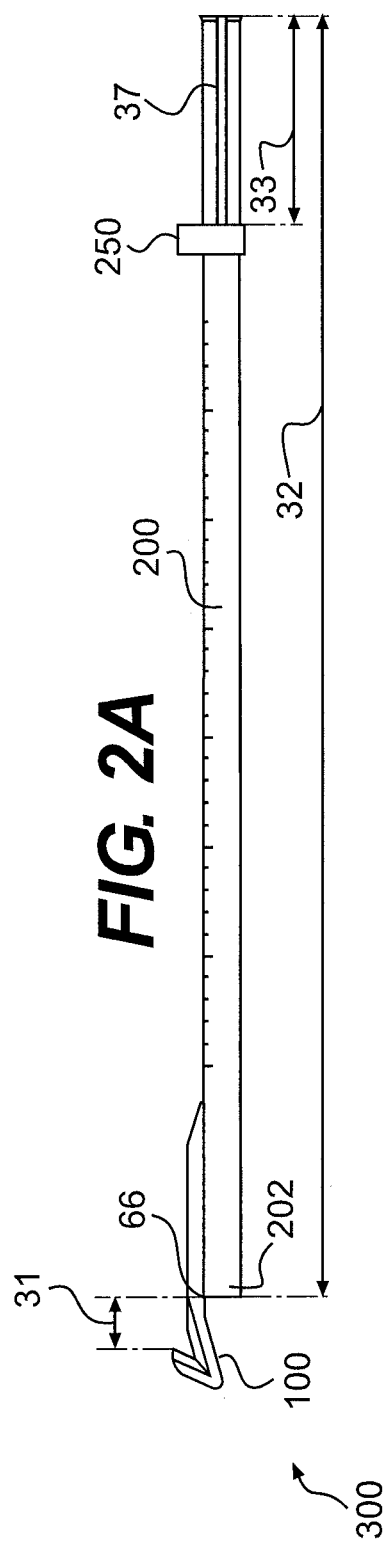
FIGS. 2A-D illustrate an endoscopic knife assembly.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper,"

"lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

In endoscopic surgery, it is sometimes undesirable or impractical to perform a cut of a tissue using a blade that is pushed forward outward from the end of a cannula to make the cut in a forward direction. This may be due to a variety of factors including, but not limited to, the proximity of the tissue to be cut (target tissue) to another tissue or an organ distal to the target tissue from that cannula, a lack of tension in the target tissue that would allow the blade to push the target tissue away from the cannula or the flexibility of the target tissue, for example.

Accordingly, the present application fills a need in the art by providing a "hook blade." The blade described herein is a low-profile blade that lacks forward facing cutting surfaces. The cutting surfaces of the blade are instead located on the trailing edge of an arm that protrudes upward from the main body of the blade (upper cutting surface) and on the forward portion of the upper surface of the main body of the blade (lower cutting surface). The arm of the blade is additionally angled back towards the main body of the blade, forming a hook. Additionally, that forward portion of the main body of the blade comprising the lower cutting surface is angled downward in front of the knife tube upon which it is mounted.

This downward angle allows the hook blade described herein to maintain a low profile such that it can be used with a slotted cannula and does not require a mechanical means for extending the blade out the side of the knife tube, as required by some other rearward-facing endoscopic cutting devices. The presently described low-profile hook blade therefore provides several advantages over other devices including, but not limited to, the lack of moving parts required to raise the blade out of the side of the knife tube reducing the risk of malfunction or failure of the cutting instrument. An additional advantage of the present low-profile hook blade design is that the lack of said moving parts and the obligatory linkages and apparatus required to operate the extension of the blade allows the knife tube to be hollow. This allows the practitioner to extend an endoscopic camera through the hollow knife tube to allow direct visualization of the tissue and blade before, during and after the cutting of the target tissue.

The design of the present low-profile hook blade is such that it is usable in endoscopic surgery in a manner that allows the practitioner to extend the blade through the cannula and past the target tissue without damage to surrounding tissue and/or organs. The blade is then positioned distal to the target tissue such that the target tissue can be drawn into the hook formed by the upper and lower cutting surfaces. The hook blade apparatus is then drawn back towards and into the cannula to effect a cut of the target tissue. The downward angle of the lower cutting surface portion of the main body of the blade and the backward angle of the arm assist in drawing the target tissue into the hook structure of the blade.

One aspect of the present application relates to a hook blade for an endoscopic knife assembly, comprising: an arm having a forward edge, a trailing edge and an upper cutting surface located on the trailing edge; a main body having an upper edge, a lower edge, a distal section, a proximate section, and a lower cutting surface located on the upper edge of the distal section; wherein the distal section of the main body angles downward from the proximate section of the main body, forming a downward angle with the proximate section of the main body, wherein the arm protrudes from the distal section of the main body and extends back towards the main body in a hook-like manner, forming a hook angle with the proximate section of the main body, and wherein the upper cutting surface and the lower cutting surface meets at a crotch forming a cutting angle between the two cutting surfaces.

In one particular embodiment, the hook angle is between about 55 degrees and about 75 degrees. In a further embodiment, the hook angle is about 65 degrees.

In another particular embodiment, the cutting angle is between about 40 degrees and about 60 degrees. In a further embodiment, the cutting angle is about 50 degrees.

In another particular embodiment, the downward angle is between about 150 degrees and about 175 degrees. In a further embodiment, the downward angle is between about 165 degrees.

In one particular embodiment, the proximate section of the main body has a tapered end.

In another particular embodiment, the main body comprises a notch on the lower edge to engage with a knife tube.

In another particular embodiment, the arm comprises an upper radius on the upper end of the forward edge to prevent the forward edge from damaging tissue as the hook blade is advanced from a cannula. In a further embodiment, the arm further comprises a lower radius on the lower end of the forward edge to prevent the forward edge from damaging tissue as the hook blade is advanced from a cannula.

In another particular embodiment, the hook blade has a total vertical height in the range of about 4 mm to about 5 mm.

Another aspect of the present application relates to an endoscopic knife assembly, comprising: a knife tube having a distal end and a proximate end; a hook blade attached to the distal end; and an alignment ring attached near the proximate end, wherein the hook blade comprises an arm having a forward edge, a trailing edge and an upper cutting surface located on the trailing edge; a main body having an upper edge, a lower edge, a distal section, a proximate section, and a lower cutting surface located on the upper edge of the distal section; wherein the distal section of the main body angles downward from the proximate section of the main body, forming a downward angle with the proximate section of the main body, wherein the arm protrudes from the distal section of the main body and extends back towards the main body in a hook-like manner, forming a hook angle with the proximate section of the main body, and wherein the upper cutting surface and the lower cutting surface meets at a crotch forming a cutting angle between the two cutting surfaces.

In another particular embodiment, the knife tube comprises one or more slots at the proximate end for the attachment of a locking assembly to the knife tube and alignment ring.

In another particular embodiment, the slots are located on a plane that is perpendicular to the hook blade attached to the distal end of the knife tube.

In another particular embodiment, the knife tube is marked on the top or side surface with gradations.

In another particular embodiment, the alignment ring comprises a flattened surface that is positioned perpendicular to the hook blade attached to the distal end of the knife tube.

In another particular embodiment, the hook blade is welded to the knife tube.

Another aspect of the present application relates to an instrument kit for implementing an endoscopic surgical procedure comprising: an endoscopic knife assembly comprising a hook blade, a knife tube and an alignment ring, wherein the blade comprises an upper cutting surface located on a trailing edge of an arm and a lower cutting surface located on an upper edge of a main body of the blade, the cutting surfaces meeting at an angle at a crotch; and a slotted cannula for endoscopic surgical procedures, wherein the endoscopic knife assembly is insertable into the slotted cannula.

In one particular embodiment, the main body of the blade comprises a notch on a lower edge of the main body to engage with the knife tube.

Another aspect of the present application relates to a method for a performing an operative procedure on a target tissue in a subject, comprising: making an incision to establish an entry portal, inserting a cannula having open proximal and distal ends, inserting an endoscope into the cannula, said endoscope comprising an endoscopic knife assembly having a hook blade, advancing said endoscope so that the hook blade moves distal to and is in contact with the target tissue, operatively engaging the target tissue with the hook blade, and withdrawing the hook blade back towards the cannula to perform the operative procedure on the target tissue.

In one particular embodiment, the operative procedure is an endoscopic surgical procedure selected from the group consisting of carpal tunnel release, cubital tunnel release, plantar fascia release, lateral release for patella realignment, release of the extensor tendons, release of the posterior and other compartments of the leg, and forearm fascial release.

In another particular embodiment, the cannula is a clear cannula.

In another particular embodiment, the cannula comprises an open slot extending along the length of the cannula.

In another particular embodiment, the inserting of said endoscope comprising an endoscopic knife assembly having a hook blade is preceded by the insertion of another endoscope comprising a means for visualization of the target tissue. In a further embodiment, the cannula is a clear cannula. In a further embodiment, the method further comprises visualization of anatomic structures surrounding the cannula.

In another particular embodiment, the establishing an entry portal comprises making an incision.

One aspect of the present application is a scope-mounting blade or endoscopic knife assembly for endoscopic surgery. The knife assembly comprises a hook blade, a knife tube and an alignment ring. The assembly is assembled by affixing the alignment ring and the blade onto the knife tube.

The hook blade is made from materials commonly used for surgical blades or scalpels, such materials include, but are not limited to, hardened and tempered steel, stainless steel, high carbon steel, titanium, alloys and ceramic. In one embodiment, the blade is made from SAE 440A stainless steel. In a preferred embodiment, the blade is made from Hitachi GIN-5 SST-MODIFIED 440-A stainless steel. The blade is optionally flash electropolished. The cutting edges are machine finished and must be sharp. In a particular embodiment, the steel of the blade is heat-treated to Rockwell C hardness of about 50-72. In a more particular embodiment, the steel of the blade is heat-treated to Rockwell C hardness of 58-64.

An embodiment of the hook blade is shown in FIGS. 1A-1F. As shown in FIG. 1A, the hook blade 100 comprises an arm 50 having a forward edge 52 and a trailing edge 54, and a main body 60 having an upper edge 62 and a lower edge 64. The upper cutting surface 1 and the lower cutting surface 2 are formed on the trailing edge 54 of the arm 50 and the upper edge 62 of the main body. The arm 50 is oriented in a hook configuration trailing an arm 50 of the blade 100. The upper cutting surface 1 and the lower cutting surface 2 meet at a central crotch 5 and form a cutting angle 4 between the two surfaces. The cutting surfaces 1 and 2 are sharp cutting surfaces, while no other surfaces of the hook blade 100 are intended to be cutting surfaces.

In one embodiment, the cutting angle 4 is between about 40 and about 60 degrees. In another embodiment, the cutting angle 4 is between about 45 and about 55 degrees. In another embodiment, the cutting angle 4 is about 50 degrees.

Referring now to FIG. 1B, the distal section 80 of the main body 60 extends downward and forms a downward angle 8 with the proximal section 70 of the main body 60. In certain embodiments, the downward angle 8 is between about 150 and about 175 degrees. In other embodiments, the downward angle 8 is between about 160 and about 170 degrees. In yet another embodiment, the downward angle 8 is about 165 degrees.

The arm 50 protrudes upward from the distal section 80 and angles back towards the main body in a hook-like manner, forming a hook angle 56 with the proximate section 70 of the main body 60. In one embodiment, the hook angle 56 is between about 55 and about 75 degrees. In another embodiment, the hook angle 56 is between about 60 and about 70 degrees. In another embodiment, the hook angle 56 is about 65 degrees.

In one embodiment, the width 6 of the arm 50 is between about 1.5 and about 2.0 mm. In another embodiment, the width 6 is between about 1.65 and 1.85 mm. In another embodiment, the width 6 is about 1.778 mm.

Referring again to FIG. 1B, in certain embodiments, the upper end of the forward edge 52 of the arm 50 has an upper radius 10 in order to prevent it from damaging tissue as the hook blade 100 is advanced from a cannula. In one embodiment, the upper radius 10 has a radius measurement of between about 1.0 mm and 2.5 mm. In another embodiment, the upper radius 10 has a radius measurement of about 2.032 mm.

In other embodiments, the lower end of the forward edge 52 of the arm 50 has a lower radius 11 in order to prevent it from damaging tissue as the hook blade apparatus is advanced from the cannula. In one embodiment, the lower radius 11 has a radius measurement between about 4 mm and 10 mm. In another embodiment, the lower radius 11 has a radius measurement of about 0.635 mm.

In certain embodiments, the distance 12 between the upper radius 10 and the lower radius 11 on the forward edge 52 of the arm 50 is between about 2.5 mm and 2.8 mm. In one embodiment, the distance 12 is about 2.62 mm.

Referring again to FIG. 1B, in certain embodiments, the arm 50 is angled back such that the horizontal distance 13 in a plane with the main body 60 of the blade 100 from the most forward point on the lower radius 11 to the top and farthest back point on cutting surface 1 is between about 3.4 and 3.8 mm. In one embodiment, the horizontal distance 13 is between about 3.5 and 3.7 mm. In another embodiment, the horizontal distance 13 is about 3.63 mm.

In certain embodiments, the height 15 of the proximate section 70 of the main body 60 is between about 1 mm and about 1.8 mm. In one embodiment, the height 15 is between about 1.2 mm and about 1.6 mm. In another embodiment, the height 15 is between about 1.3 mm and about 1.4 mm. In another embodiment, the height 15 is about 1.42 mm.

In certain embodiments, the vertical distance 16 between the top and farthest back point on cutting surface 1 and the bottom edge 64 of the proximate section 70 is between about 2.4 mm and about 3.0 mm. In one embodiment, the vertical distance 16 is between about 2.6 mm and about 2.8 mm. In another embodiment, the vertical distance 16 is about 2.69 mm. In order to insure that, during manufacture, the hook blade 100 is consistently joined to the knife tube 200 in the same location, the lower edge 64 of the main body 60 comprises a notch 66. During assembly of the endoscopic knife assembly, the notch 66 is butted against the front of the knife tube. Following the positioning of the blade on the knife tube, the blade 100 is laser welded all around to the knife tube. In one embodiment, the strength of the weld is tested by applying torque to the unit, for example about 10 in-lbs of torque. In certain embodiments, the depth 21 of the notch 66 is between about 0.025 mm and about 0.18 mm. In one embodiment, the depth 21 of the notch 66 is between about 0.051 mm and about 0.1524 mm. In another embodiment, the depth 21 of the notch 66 is about 0.102 mm.

Additionally, in certain embodiments, the horizontal distance 22 between the notch 66 and the focus of angle 8 is between about 1.6 mm and about 2.1 mm, preferably about 1.85 mm. In another embodiment, the horizontal distance 23 between the notch 66 and the top and farthest back point on cutting surface 1 is between about 3.0 mm and about 7.0 mm, preferably between about 4.0 mm and about 5.5 mm, and more preferably about 4.78 mm or 4.826 mm. In yet another embodiment, the horizontal distance 24 between the notch 66 and the top and farthest back point on cutting surface 2 is between about 2.8 mm and about 3.3 mm, preferably about 3.05 mm.

In order to prevent the hook blade from catching on the interior surface of the cannula when the blade 100 is drawn backwards through the cannula tube, the blade 100 has a tapered trailing edge 27. In one embodiment, the horizontal length of the tapered trailing edge 27 is between about 2.5 mm to about 10 mm, more particularly about 3.0 mm to about 5.0 mm. In another embodiment, the horizontal length of the tapered trailing edge 27 is about 3.81 mm. In some embodiments, the tapered trailing edge 27 has a blunt end, with a depth 28 of between about 0.1 mm to about 0.4 mm, more particularly about 0.254 mm.

Referring now to FIG. 1C, in certain embodiments, the total length 14 of the blade 100 from the leading point of the lower radius 11 to the trailing end of the proximate section 70 is between about 15 mm and about 40 mm. In one embodiment, the total length 14 of the blade 100 is between about 20 mm and about 330 mm. In another embodiment, the total length 14 of the blade 100 is about 26.4 mm.

Referring now to FIG. 1D, in certain embodiments, the vertical distance 19 between the center of the lower radius 11 and the bottom edge 64 of the main body 60 (where it is affixed to the knife tube) is between about 0.9 mm and about 1.2 mm. In one embodiment, the vertical distance 19 is between about 1.0 mm and about 1.1 mm. In another embodiment, the vertical distance 19 is about 1.04 mm.

In some embodiments, the upper cutting surface 1 and lower cutting surface 2 form a sharp angle at the crotch 5. In other embodiments, the upper cutting surface 1 and lower cutting surface 2 meet at the crotch 5 with a ground curved corner. In one embodiment, the grinding of the upper cutting surface 1 and lower cutting surface 2 cutting surfaces where they meet at the crotch 5 has a maximum radius of about 0.65 mm. In a particular embodiment, the grinding at the crotch 5 has a maximum radius of about 0.5 mm. In a more particular embodiment, the grinding at the crotch 5 has a maximum radius of 0.381 mm.

Referring again to FIG. 1D, in one embodiment, the horizontal distance 25 between the notch 66 and the focus of radius 11 is between about 7.5 mm and about 8.0 mm, preferably about 7.77 mm.

In order to maintain uniform measurement of the gradations on the knife tube 200 and the cutting surfaces of the hook blade 100, the horizontal distance 26 between the notch 66 and the crotch 5 is preferably 5.41 mm. Alternatively, a horizontal distance 26 can be chosen for a particular model or lot of the hook blade 100 within a range of about 2.5 mm to about 10 mm.

Referring again to FIG. 1D, in a particular embodiment, the vertical distance 20 between the crotch 5 and the bottom edge 64 of the main body 60 (where it is affixed to the knife tube) is between about 0.6 mm and about 0.9 mm. In another embodiment, the vertical distance 20 is between about 0.7 mm and about 0.8 mm. In a more particular embodiment, the vertical distance 20 is about 0.762 mm.

FIG. 1E shows a cross-sectional view of the distal section 80 of the main body 60 from line 3-3 in FIG. 1D. In one embodiment, the cross-sectional depth 82 of the distal section 80 is between about 1.5 mm and 2.0 mm. In another embodiment, the cross-sectional depth 82 of the distal section 80 is between about 1.6 mm and 1.9 mm. In another embodiment, the cross-sectional depth 82 of the distal section 80 is about 1.778 mm.

Similarly, in one embodiment, the cross-sectional depth of the arm 50 (i.e., the cross-section from line 3'-3' in FIG. 1D) is between about 1.5 mm and 2.0 mm. In another embodiment, the cross-sectional depth 82 of the arm 50 is between about 1.6 mm and 1.9 mm. In another embodiment, the cross-sectional depth 82 of the arm 50 is about 1.778 mm.

Referring again to FIG. 1E, in certain embodiments, the cutting surfaces 1 and 2 each contains a subsurface a and a subsurface b that forms a surface angle 29 with the subsurface a. In certain embodiments, the cutting angle 29 of the cutting surfaces 1,2 is between about 35 degrees and about 45 degrees, more particularly about 40 degrees. In certain embodiments, the subsurfaces a and b each have a width 30 that is between about 0.8 mm and about 1.0 mm, more particularly about 0.91 mm.

Referring now to FIG. 1F, in certain embodiments, the total vertical height 17 of the hook blade 100 from the bottom of radius 11 to the top and farthest back point on cutting edge 1 is between about 4.0 mm and about 5.0 mm. In one embodiment, the total vertical height 17 is between about 4.35 mm and about 4.65 mm. In another embodiment, the total vertical height 17 is about 4.445 mm.

In certain embodiments, the thickness 18 of the hook blade 100 is between about 0.50 mm and about 0.75 mm. In one embodiment, the thickness 18 of the hook blade 100 is between about 0.60 mm and about 0.67 mm. In another embodiment, the thickness 18 of the hook blade is about 0.635+/−0.013 mm.

Referring again to FIG. 1F, in certain embodiments, the distal section 80 of the main body 60 extends below the bottom edge 64 of the main body 60 (where it affixes to the knife tube) a distance 9 of between about 1.5 and 1.9 mm.

In another embodiment, the distance 9 is between about 1.6 and about 1.8 mm. In another embodiment, the distance 9 is about 1.68 mm.

FIGS. 2A-2D show a hook-blade assembly 300 with a hook blade 100 mounted on a knife tube 200. As shown in FIG. 2A, the hook blade 100 is attached to the knife tube 200, such that the notch 66 of the blade 100 is butted up against the distal end 202 of the knife tube 200. In one embodiment, the hook blade 100 is welded to the knife tube 200.

In one embodiment, the top and farthest back point of upper cutting surface 1 extends a distance 31 of about 3.0 mm to about 7.0 mm, more particularly about 4.0 mm to about 5.5 mm forward of the knife tube. In a most particular embodiment, the distance 31 is about 4.826 mm or 4.78 mm.

In a particular embodiment, the length 32 of the knife tube 200 is from about 100 mm to about 140 mm, preferably from about 114.3 mm to about 119.4 mm. In a more preferred embodiment, the length 32 of the knife tube 200 is about 116.84 mm.

Figure 2B:
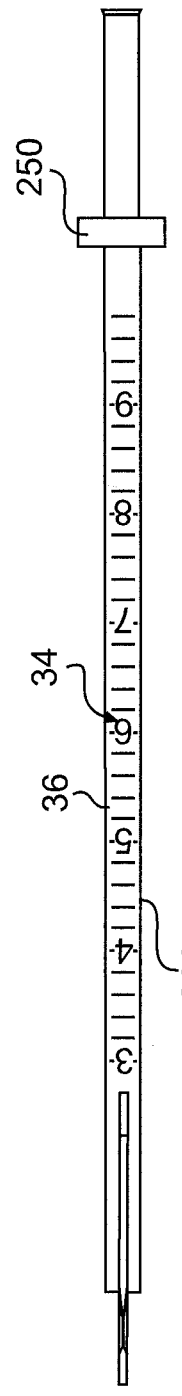
Figure 2C:
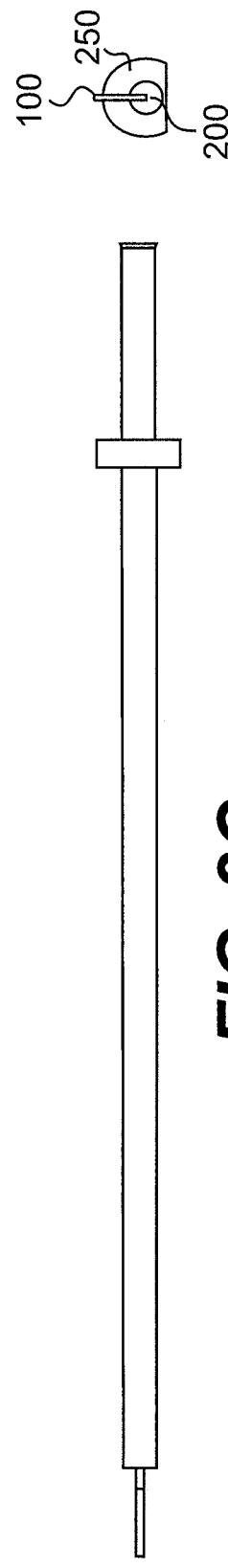
Figure 2D:

The knife tube 200 can optionally be marked on the top or side surface with gradations as exemplified in FIG. 2B to show the distance to the crotch 5 of the cutting surfaces. For example, major gradations 34 can be made to show each centimeter in distance from the crotch 5, with minor gradations 36 between them to show each 1, 2, 2.5 or 5 millimeters. While the gradations can be applied to the knife tube by any means known in the art, it is preferable to lasermark the gradations on the knife tube 200 for accuracy and permanence. Additionally, the knife tube 200 can also be marked in a similar manner with additional information, for example on the bottom or a side surface of the knife tube 200. Exemplary markings may include, but are not limited to, a maker's mark, part number, lot number and an indication that the endoscopic knife assembly is intended for only a single use (see, e.g., FIG. 2C).

Referring again to FIG. 2A, an alignment ring 250 is affixed near the proximate end of the knife tube 200. In one embodiment, the alignment ring 250 is affixed in position on the knife tube 200 using USP Class VI gamma irradiation and steam resistant epoxy adhesive during assembly. Preferably, a two part epoxy such as MASTERBOND EP42 HT™ or ARMSTRONG C-7™, or a suitable equivalent thereof is used. In one embodiment, the distance 33 between the alignment ring 250 and the proximate end of the knife tube 200 is between about 15 mm and about 25 mm. In another embodiment, the distance 33 is between about 18.67 mm and about 19.43 mm. In another embodiment, the distance 33 is about 19.05+/−0.38 mm.

The knife tube further comprises slots 37 in the proximate end that are positioned on the sides of the knife tube 200, perpendicular to the blade mounted on the top of the knife tube. The slots 37 preferably extend forward to where the alignment ring 250 is affixed to the knife tube 100.

The slots and alignment ring provide an attachment point for a locking device, in order to mount an endoscope to the scope-mounting blade or endoscopic knife assembly.

FIGS. 3A-E show perspective views of a knife tube 200 without an affixed blade or alignment ring and without gradations. Referring now to FIG. 3A, in one embodiment, the outer diameter 38 of the knife tube 200 is between about 2.8 mm and about 3.6 mm, preferably between about 3.073 mm and about 3.175 mm. In a more preferred embodiment, the outer diameter 38 is about 3.124 mm.

Referring again to FIG. 3A, in another embodiment, the knife tube 200 has a flared proximate end 40. In one embodiment, about 0.2 to about 0.5 most proximate millimeters of the knife tube 200 are flared. In another embodiment, about the 0.381 most proximate millimeters of the knife tube 200 are flared. In another embodiment, the flared proximate end 40 has a flare angle 41 of about 20 to 40 degrees, more preferably about 30 degrees. In still another embodiment, the outer diameter 42 of the flared proximate end 40 of the knife tube is about 0.25 mm to about 0.45 mm, more particularly about 0.356 mm.

Referring now to FIG. 3B, the inner diameter 39 of the knife tube 200 is such that an endoscope camera can be inserted into the knife tube in order to show the blade and the target tissue during a procedure. In one embodiment, the inner diameter 39 is between about 2 mm and about 3.5 mm. In a particular embodiment, the inner diameter 39 is between about 2.769 mm and about 2.87 mm. In a more particular embodiment, the inner diameter 39 is about 2.819 mm.

In one embodiment, the slots 37 have a width 43 of between about 0.4 mm and about 1.1 mm wide, more particularly between about 0.533 mm and about 0.914 mm wide. Even more particularly, the width 43 of the slots is about 0.6604 mm.

FIGS. 4A-D show an embodiment of the alignment ring 250 of the endoscopic knife assembly of the application. Referring now to FIG. 4A, in one embodiment, the alignment ring 250 has a flattened surface 252 that, when the alignment ring 250 is affixed to the knife tube 200, is oriented on the bottom of the knife tube 200, i.e., opposite of the mounting of the blade 100. When the endoscopic knife assembly is fully assembled, the flattened surface 252 of the alignment ring forms a right angle with the vertical orientation of the affixed blade 100, as depicted in FIG. 4B.

In one embodiment, the inner diameter 44 of the alignment ring, which must fit on the outside of the knife tube 200, is between about 2.8 mm and about 3.7 mm, particularly between about 3.15 mm and about 3.175 mm. In a more particular embodiment, the inner diameter 44 is about 3.15 mm.

In a particular embodiment, the outer diameter 45 of the alignment ring is between about 6 mm and about 10 mm, preferably between about 7.569 mm and about 7.671 mm. In a more preferred embodiment, the outer diameter 45 is about 7.62 mm.

As shown in FIG. 4B, in one embodiment, the distance 46 between the inner opening of the alignment ring and the flattened surface 252, on a line perpendicular to the flattened surface 252, is between about 0.25 mm and about 0.5 mm, preferably between about 0.330 mm and about 0.432 mm. In more preferred embodiment, the distance 46 is about 0.381 mm.

Referring to FIG. 4C, showing a side view of the alignment ring, and FIG. 4D, showing a view from the top of the alignment ring, in one embodiment, the alignment ring 250 has a thickness 47 of between about 1.0 mm and about 4.0 mm. In a particular embodiment, the thickness 47 is between about 2.0 mm and about 3.0 mm. In a more particular embodiment, the thickness 47 is about 2.54 mm.

The hook blade 100 and the endoscopic knife assembly 300 described above may be readily applied to surgical procedures such as, but not limited to, carpal tunnel release; cubital tunnel release, plantar fascia release, lateral release for patella realignment, release of radial tunnel, release of pronatar teres, release of trigger finger, release of lacertous fibrosis, release of the extensor tendons for lateral epicondylitis (tennis elbow), release of medial epicondylitis (golfer's elbow), and release of fascial compartments in the upper and lower extremity.

Another aspect of the present application relates to an instrument kit for implementing an endoscopic surgical procedure. The instrument kit contains an endoscopic knife assembly having a hook blade and a cannula guide member including a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In one embodiment, the instrument kit further includes an endoscope sized for insertion into the cannula guide member for direct visualization of an operative site.

In another embodiment, the endoscope is capable to carry a cutting instrument at a leading end.

In another embodiment, the instrument kit further includes a second cutting instrument mountable to the leading end of the endoscope.

In another embodiment, the instrument kit further includes a second endoscope with a second cutting instrument mounted at a leading end of the second endoscope. The second endoscope is insertable into the cannula guide member such that the cutting instrument protrudes through the open slot in the cannula guide member. The second cutting instrument may be an endoscopic knife assembly having a hook blade or an endoscopic knife assembly having another type of blade including, but not limited to, a blade comprising an upper and a lower cutting surface on the forward edge of the blade, said cutting surfaces meeting at an angle at a crotch.

In another embodiment, the instrument kit further includes a depth gauge mountable to a leading end of the endoscope.

In another embodiment, the instrument kit further includes a rasp member sized for insertion into the cannula guide member.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

Another aspect of the present application relates to a method for implementing a uniportal endoscopic surgical procedure using an endoscopic knife assembly having a hook blade of the present application. In one embodiment, the method includes the steps of making an incision on a patient in need of such endoscopic surgical procedure at a location proximate an operation site to establish an entry portal, inserting an elongate insertion member into a longitudinal bore of an elongate transparent cannula having open proximal and distal ends and an open slot extending along the length of the cannula, the elongate insertion member being configured to form a smooth exterior surface at the open distal end of the cannula when fully inserted into the cannula; introducing the distal end of the cannula/insertion member combination into the entry portal and advancing the combination a predetermined distance relative to the operation site; withdrawing the insertion member while permitting the cannula to remain in place at the operation site; inserting a first endoscope into the cannula for direct visualization of anatomic structures surrounding the cannula and positioning of the cannula at the operative site; withdrawing the first endoscope from the cannula; mounting an endoscopic knife assembly having a hook blade on a leading end of a second endoscope; inserting the endoscope with the endoscopic knife assembly having a hook blade into the cannula such that the hook blade protrudes into the open slot in the cannula, and advancing the second endoscope so that the endoscopic knife assembly having a hook blade moves distal to and is in contact with a target tissue at the operation site; operatively engaging the target tissue with the endoscopic knife assembly having a hook blade while withdrawing the latter back towards the cannula under direct visualization through the second endoscope so as to perform an operative procedure on the target tissue; withdrawing the second endoscope and the endoscopic knife assembly having a hook blade from the cannula; withdrawing the cannula through the entry portal; and suturing the incision.

In one embodiment, the first endoscope and the second endoscope are the same endoscope. In another embodiment, the first endoscope and the second endoscope are different endoscopes.

The cannula can be inserted into the tissue through a small opening and advanced to a surgical site, thus forming a passageway towards the surgical site. The passageway allows the insertion of the endoscope and endoscopic knife assembly having a hook blade to the surgical site without further damages to the surrounding tissues. The endoscopic knife assembly having a hook blade and a slotted cannula can be used in endoscopic surgical procedures such as carpal tunnel release, cubital tunnel release, plantar fascia release, lateral release for patella realignment, release of the extensor tendons for lateral epicondylitis (tennis elbow), release of the posterior and other compartments of the leg, and the forearm fascial release for fascial compartment syndrome.

The contents of all references, patents and published patent applications cited throughout this application, as well as the Figures and Tables are incorporated herein by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A hook blade for an endoscopic surgical assembly comprising the blade and a tube marked with gradations showing distance, wherein the blade comprises:
   an arm having a forward edge that is a non-cutting surface, a trailing edge and an upper cutting surface located on the trailing edge;
   a main body having an upper edge, a lower edge, a distal section, a proximate section, and a lower cutting surface located on the upper edge of the distal section;
   wherein the distal section of the main body angles downward from the proximate section of the main body, forming a downward angle with the proximate section of the main body;
   wherein the arm protrudes from the distal section of the main body, forming a hook angle with the proximate section of the main body, wherein the upper cutting surface and the lower cutting surface meet at a crotch forming a cutting angle between the two cutting surfaces, wherein the main body comprises a notch on the lower edge, wherein the notch is on an opposite side of the blade from the upper cutting surface of the arm, wherein the lower edge that includes the notch is in direct contact with a cylindrical surface of the tube marked with the gradations, and wherein during a surgical procedure, relative positions of the gradations with respect to a location of the direct contact with the notch are visible.

2. The hook blade of claim 1, wherein the downward angle is between about 150 degrees and about 175 degrees.

3. The hook blade of claim 1, wherein the proximate section of the main body has a tapered end.

4. The hook blade of claim 1, wherein the arm comprises an upper radius on the upper end of the forward edge to prevent the forward edge from damaging tissue as the hook blade is advanced from a cannula.

5. The hook blade of claim 4, wherein the arm further comprises a lower radius on the lower end of the forward edge to prevent the forward edge from damaging tissue as the hook blade is advanced from a cannula.

6. The hook blade of claim 1, wherein the hook blade has a total vertical height in the range of about 4 mm to about 5 mm.

7. An endoscopic surgical assembly, comprising:
a blade; and
a tube marked with gradations showing distance,
wherein the blade comprises a distal blade portion and a planar main body,
wherein the distal blade portion angles downward from the planar main body, forming a downward angle with the planar main body;
wherein the distal blade portion and the planar main body are connected at an interface to form the blade,
wherein the blade comprises a notch formed on a lower edge of the blade at the interface between the distal blade portion and the planar main body so that the notch defines the distal portion of the blade,
wherein the planar main body extends along an axis parallel to a longitudinal centerline of the tube of the endoscopic knife assembly,
wherein the distal blade portion includes a non-cutting surface formed as a radiused top edge facing away from the planar main body, and upper and lower cutting edges meeting at a crotch at the distal blade portion and forming a cutting angle between the two cutting edges,
wherein the lower edge of the blade is on an opposite side of the blade from the radiused top edge of the distal blade portion,
wherein the notch is on an opposite side of the blade from the radiused top edge of the distal blade portion,
wherein the lower edge that includes the notch is in direct contact with the cylindrical surface of the tube marked with the gradations, and
wherein during a surgical procedure, relative positions of the gradations with respect to a location of the direct contact with the notch are visible.

8. The endoscopic surgical assembly of claim 7, wherein the tube comprises one or more slots at a proximate end for the attachment of a locking assembly to the tube.

9. The endoscopic surgical assembly of claim 8, wherein the slots are located on a plane that is perpendicular to the blade attached to a distal end of the tube.

10. The endoscopic surgical assembly of claim 7, wherein the tube is marked on the top or side surface with gradations.

* * * * *